United States Patent
West

(10) Patent No.: US 6,263,224 B1
(45) Date of Patent: Jul. 17, 2001

(54) HANDLE FOR CATHETER ASSEMBLY WITH MULTIFUNCTION WIRE

(75) Inventor: Scott H. West, Tracy, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/578,619

(22) Filed: May 25, 2000

Related U.S. Application Data

(62) Division of application No. 09/382,352, filed on Aug. 25, 1999, which is a division of application No. 08/920,340, filed on Aug. 27, 1997, now Pat. No. 5,987,344, which is a continuation-in-part of application No. 08/694,363, filed on Aug. 8, 1996, now Pat. No. 5,826,576.

(51) Int. Cl.$^7$ ........................................................ A61B 5/04
(52) U.S. Cl. ........................... 600/373; 606/41; 607/122; 600/585; 604/528
(58) Field of Search .................................. 600/372, 373, 600/585; 607/119, 122; 606/41; 604/204, 528

(56) References Cited

U.S. PATENT DOCUMENTS 5,487,757  1/1996  Truckai et al. .

Primary Examiner—Linda C. M. Dvorak
Assistant Examiner—David Ruddy
(74) Attorney, Agent, or Firm—Beth L. McMahon

(57) ABSTRACT

Multifunction and radial deflection wires (66, 64) extend from a catheter shaft (8) and into a handle (4). The multifunction wire is pulled and pushed longitudinally and is rotated about its axis to change the stiffness of and to laterally deflect the tip portion (12). A curve size manipulator (32) on the handle body (24) moves the multifunction wire longitudinally but does not hinder its rotational movement. Rotation of a lateral deflection manipulator (38) on the handle causes the proximal end (70) of the multifunction wire to rotate about its own axis; the free longitudinal movement of the proximal end is unhindered. Any initial corkscrewing or other deflection of the tip portion can be removed at assembly by rotating the proximal end (68) of the radial deflection wire. The longitudinal movement of the manipulators can be limited by movable stops (120). The longitudinal positions of the abutment faces (126, 128) of the stops preferably change according to their longitudinal (distal or proximal) orientation.

1 Claim, 6 Drawing Sheets

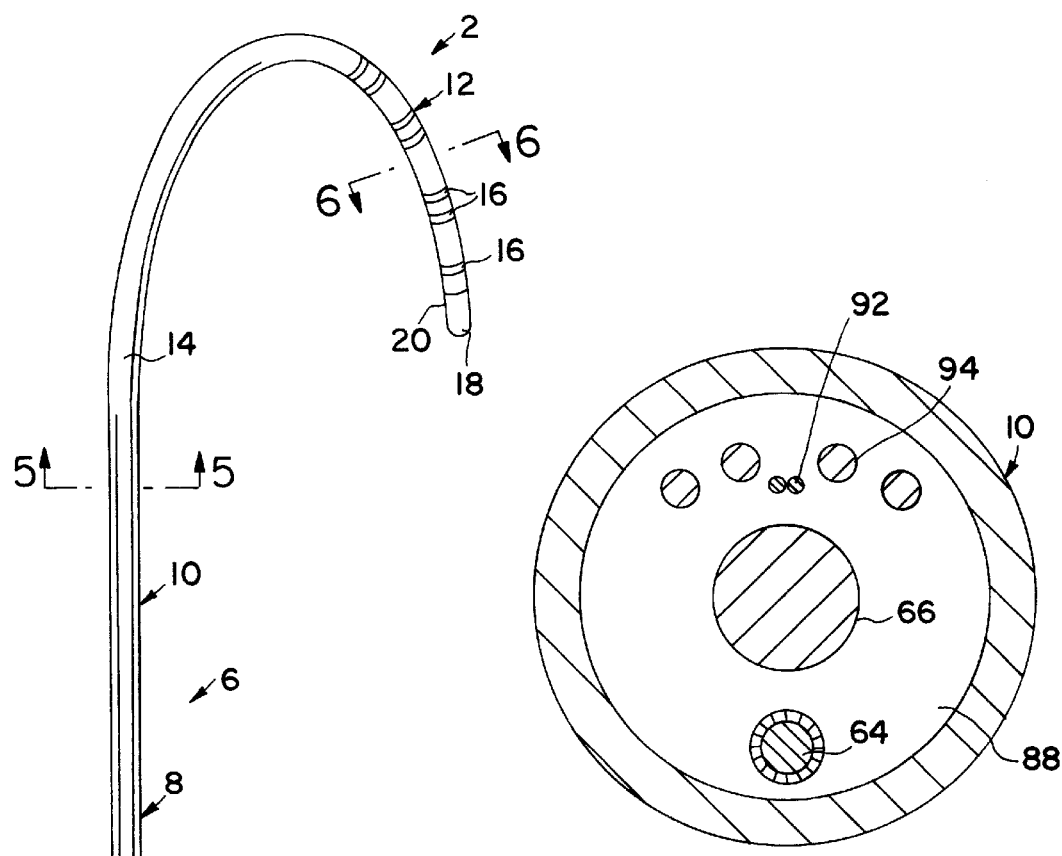
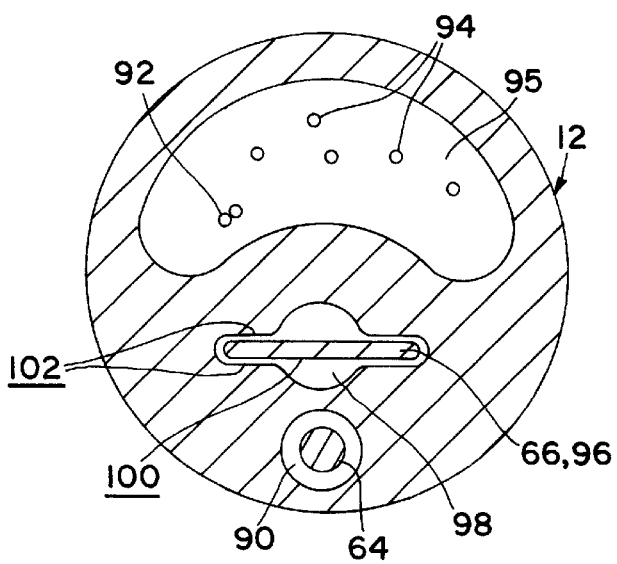

US 6,263,224 B1

HANDLE FOR CATHETER ASSEMBLY WITH MULTIFUNCTION WIRE

CROSS-REFERENCE TO RELATED APPLICATIONS

This is a divisional application of prior application Ser. No. 09/382,352 filed Aug. 25, 1999 which is a divisional of prior application Ser. No. 08/920,340, filed Aug. 27,1997 now U.S. Pat. No. 5,987,344 which is a continuation-in-part of prior application Ser. No. 08/694,363, filed Aug. 8,1996 now U.S. Pat. No. 5,826,576.

This application is related to U.S. Pat. No. 5,545,200, issued Aug. 13, 1996 entitled "Steerable Electro-physiology Catheter." This application is a continuation-in-part of U.S. patent application Ser. No. 08/694,363, filed Aug. 8, 1996, entitled "Electrophysiology Catheter with Multi-Function Wire and Method for Making. " The disclosure of each is incorporated by reference.

BACKGROUND OF THE INVENTION

Electrophysiology catheters are designed for use in mapping and/or ablation of the heart. Electrophysiology catheters typically include a number of band electrodes mounted to the tip portion of the catheter shaft and a tip electrode at the distal end of the catheter shaft. To properly manipulate the electrodes against the target sites within a heart, the tip portion must be flexible and capable of being manipulated into a variety of shapes. U.S. patent application Ser. No. 5,487,757, entitled "Multicurved Deflectable Catheter, " the disclosure of which is incorporated by reference, discloses an electrophysiology catheter in which the tip portion can be deflected radially by pulling on a manipulator wire and also defected laterally by rotating a core wire which extends into the tip section. In addition to the manipulator and core wires, this patent discloses the use of an axially slidable stiffener wire, the distal end of which can be located at different positions along the tip portion to change the stiffness of the tip, and thus the general size of the curve in the tip.

SUMMARY OF THE INVENTION

The present invention is directed to improvements for a catheter assembly of the type having a multifunction wire. The proximal end of the multifunction wire is both rotated about its longitudinal axis and slid longitudinally. This rotational and longitudinal movement occurs when the user operates lateral deflection and longitudinal position manipulators mounted to the handle body.

The catheter assembly also includes a catheter shaft extending from the distal end of a handle body with the proximal portion of a multifunction wire extending into the handle body. The multifunction wire is pulled and pushed longitudinally and is rotated about its axis to provide multiple functions for the catheter shaft.

The longitudinal position manipulator is preferably slidably mounted to the body of the handle for movement between first and second longitudinally spaced apart positions. The longitudinal position manipulator is connected to the multifunction wire through a rotary coupling so that movement of the longitudinal position manipulator causes longitudinal movement of the multifunction wire but does not hinder the free rotational movement of the proximal portion of the multifunction wire.

The lateral deflection manipulator is preferably rotatably mounted to the body of the handle. The proximal end of the multifunction wire preferably has an elongate drive adapter which passes through a hole in a first gear; the first gear is rotatably mounted to the handle body at a fixed position aligned with the lateral defection manipulator. The lateral deflection manipulator is rotatably coupled to the first gear, and thus to the drive adapter, typically by second and third gears. The drive adapter and first gear have interfering torquing surfaces so that rotation of the lateral deflection manipulator causes the drive adapter, and thus the proximal portion of the multifunction wire, to rotate about its own longitudinal axis while not hindering the free longitudinal movement of the drive adapter through the first gear.

In addition to the multifunction wire, a radial deflection wire, for example, can also be used with the invention. The proximal end of the radial deflection wire is preferably coupled to a radial deflection manipulator in a way which permits the rotary orientation of the proximal end of the radial deflection wire to be adjusted relative to the handle. This is typically done to remove, during assembly, undesirable twisting, corkscrewing, or other deflection of the tip portion of the catheter shaft. The longitudinal movement of the longitudinal position manipulator and the radial deflection manipulator can be limited by use of movable stops which can be mounted to the handle body at a range of longitudinal positions. The longitudinal stops can be configured so that the longitudinal positions of the abutment faces of the stops change according to the orientation of the stops.

The multifunction wire preferably extends into the flexible tip portion of the catheter shaft and is freely longitudinally slidable within the tip portion. Torquing force, which creates lateral deflection of the radially deflected tip portion, is preferably transmitted from the multifunction wire to the tip portion by providing both the distal end of the multifunction wire and the multifunction wire lumen within the tip portion with interfering torquing surfaces, such as created when the two have generally complementary oblong cross-sectional shapes.

Other features and advantages of the invention will appear from the following description in which the preferred embodiment has been set forth in detail in conjunction with the accompanying drawings.

BRIEF DESCRIPTION OF THE DRAWINGS

FIG. 1 is a simplified overall view of a catheter assembly made according to the invention;

FIG. 5 is a cross-sectional view of the catheter shaft of FIG. 1 taken along line 5—5 of FIG. 1;

FIG. 6 is a cross-sectional view of the tip portion of the catheter shaft of FIG. 1 taken along line 6—6 of FIG. 1;

DESCRIPTION OF THE PREFERRED EMBODIMENT

Figure 2:
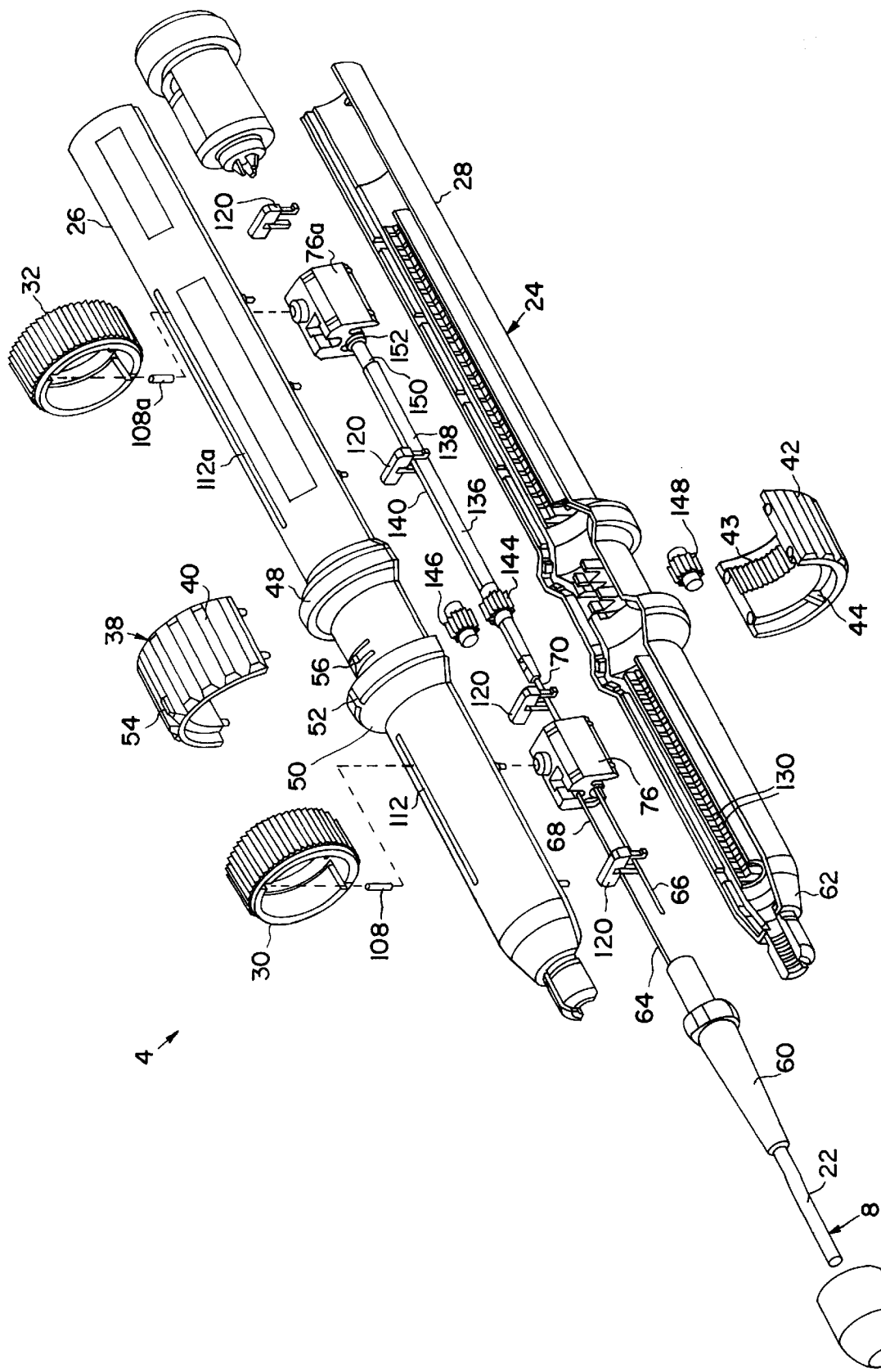
FIG. 2 is an exploded isometric view of the handle of the catheter assembly of FIG. 1.

FIG. 1 illustrates a catheter assembly 2 including a proximal end assembly or handle 4 from which a catheter 6 extends. Catheter 6 includes a catheter shaft 8 having a main, proximal portion 10 and a distal, tip portion 12 joined at a butt joint 14. Tip portion 12 is preferably more flexible than main portion 10 and has a number of electrodes 16 along its length, and typically a tip electrode 18 at the distal end 20 of catheter shaft 8. Catheter shaft 8 has a proximal end 22 mounted to and extending from handle 4.

Figure 3:
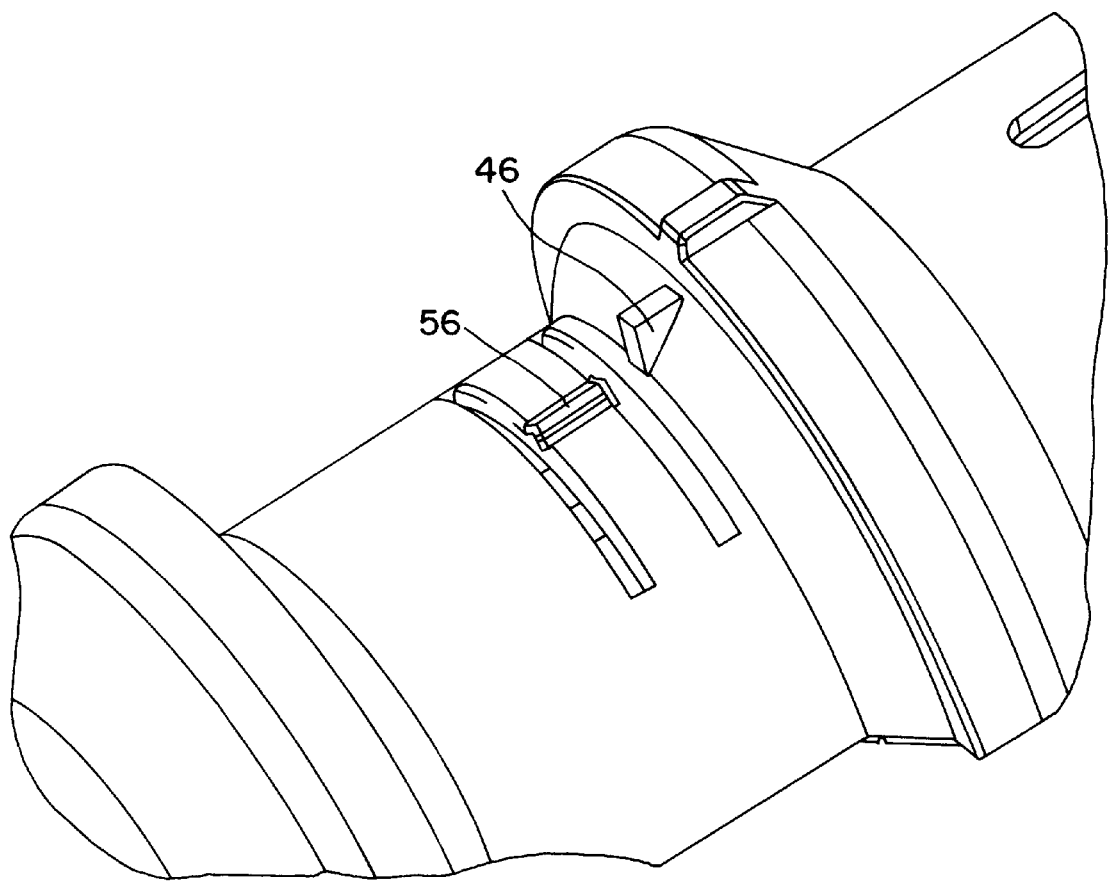
FIG. 3 is an enlarged external isometric view of the central portion of the upper body part of FIG. 2 from a reverse direction showing a spring finger and an over-rotation stop.

FIG. 2 illustrates handle 4 in more detail. Handle 4 includes a hollow body 24 comprising an upper body part 26 and lower body part 28. Handle 4 includes a radial deflection manipulator 30 and a curve size manipulator 32 both slidably mounted to handle 4 for movement along the longitudinal length of the handle, that is parallel to arrows 34, 36 of FIG. 1. Handle 4 also includes a rotatable lateral deflection manipulator 38 in the form of a split ring. Manipulator 38 includes a first split ring portion 40 and a second split ring portion 42. First and second portions 40, 42 define an internal gear 43 for purposes to be discussed below. Second split ring portion 42 has a stop 44 centered along its distal end which engages an over-rotation stop 46 formed on upper body part 26, see FIG. 3. Rotation of manipulator 38 is limited to just under 360°, that is about 180° each way from the position of FIG. 2 (when assembled), by the engagement of stops 44, 46 at either end of the travel.

Upper body part 26 has a pair of annular barriers 48, 50 which keep lateral deflection manipulator 38 properly aligned on hollow body 24. Annular barrier 50 has a neutral alignment projection 52 which aligns with a similar projection 54 on first split ring portion 40 when lateral deflection manipulator 38 is at its centered or neutral position. The user is provided additional tactile and audible indication of this centered or neutral alignment of manipulator 38 relative to body 24 by the engagement of a projection 56 formed on a spring finger 58, the spring finger being a portion of upper body part 26 between annular barriers 48, 50. Projection 56 engages a recess, not shown, formed on the inner surface of first split ring portion 40 at a location generally aligned with projection 54.

Figure 4:
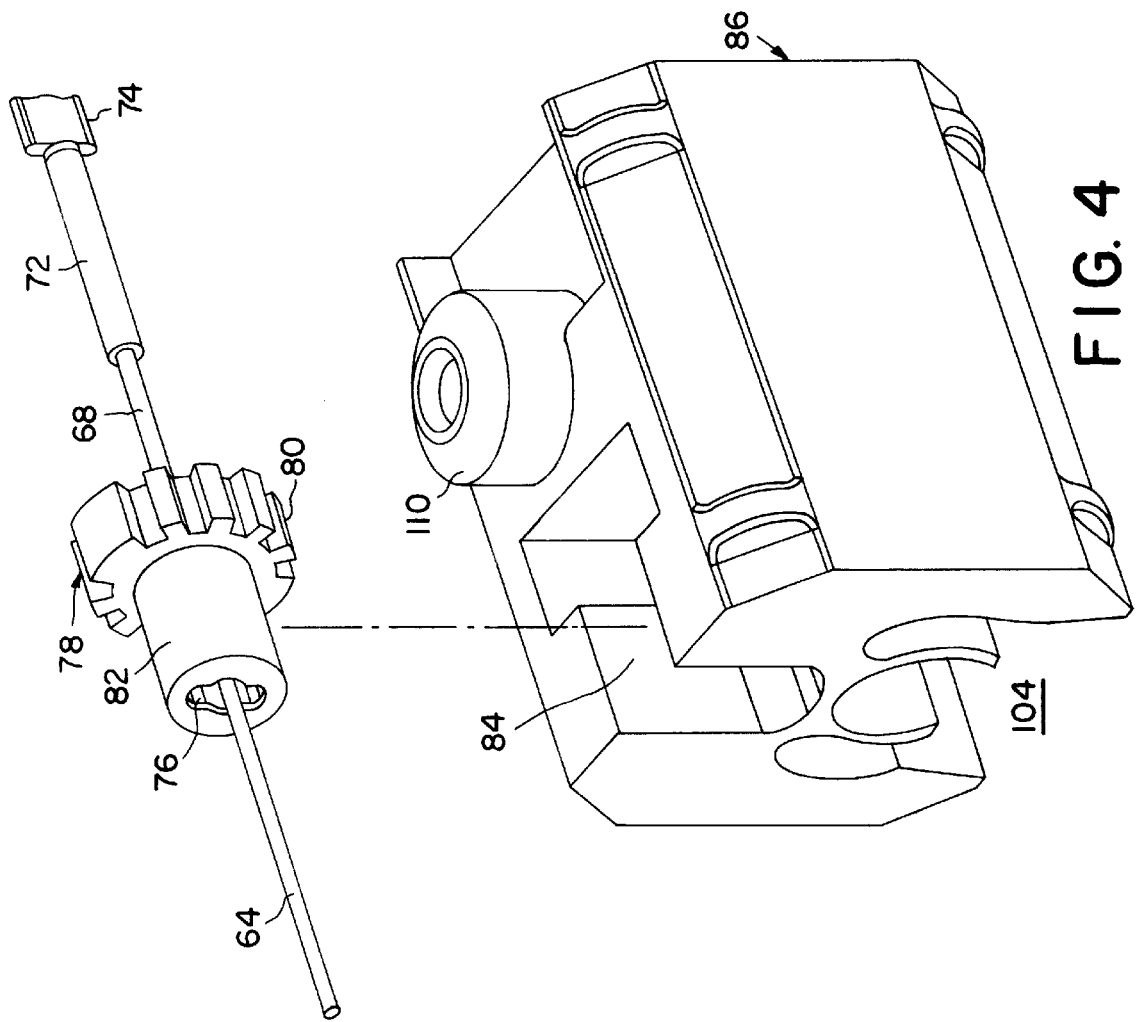
FIG. 4 is an enlarged exploded isometric view of a slider and the proximal end of the radial deflection wire before being secured to the adjustment adapter of FIG. 2.

Proximal end 22 of catheter shaft 8 extends into a strain relief 60 at the distal end 62 of body 24. Catheter 3 includes a radial deflection wire 64 and multifunction wire 66 passing through catheter shaft 8. The proximal ends 68, 70 of wires 64, 66 extend into hollow body 24. FIG. 4 illustrates proximal end 68 of radial deflection wire 64 having a section of hypotube 72 secured to distal end 68. The distal end 74 of hypotube 72 is flattened for keyed access into an oblong opening 76 formed in an adjustment adapter 78. Adjustment adapter 78 has an enlarged, serrated end 80 and a smaller diameter cylindrical end 82 sized to fit within a T-slot 84 formed in a slider 86. T-slot 84 is sized so that adjustment adapter 78 fits snugly within the T-slot through frictional engagement of the adjustment adapter in the T-slot. However, the exposed serrated end 80 of adjustment adapter 76 permits the rotary orientation of proximal end 68 of radial deflection wire 64 to be adjusted through the use of a small screwdriver or other tool which can be used to rotate adjustment adapter 78 within T-slot 84 overcoming the frictional resistance which normally prevents such rotation. This is useful because it permits, at assembly, any corkscrewing or other undesirable deflection of tip portion 12 to be removed or at least substantially reduced.

As shown in FIGS. 5 and 6, radial deflection wire 64, which is preferably coated with a lubricious material such as PTFE, passes through a main lumen 88 formed in main portion 10 of catheter shaft 8 and then through a radial deflection lumen 90 formed in tip portion 12. Radial deflection wire 64 is preferably secured to tip portion 12 at or near distal end 20 of catheter shaft 8. As can be seen from these figures, multifunction wire 66, thermocouple wires 92 and electrode wires 94 will also pass through main lumen 88. Electrode wires 94 and thermocouple wires 92 pass through an electrode wire lumen 95 within tip portion 12 while the distal end 96 of multifunction wire 66 passes through a lateral deflection lumen 98. Lateral deflection lumen 93 is sized with an enlarged central region to permit the proximal portion of multifunction wire 66 to pass through lumen 98. Otherwise, lumen 98 has a flattened shape similar to the flattened shape of distal portion 96 so that the torque transmitting, interfering torquing surfaces 100, 102 of distal portion 96 and lateral deflection lumen 98 oppose. This arrangement permits distal end 96 of multifunction wire 98 to slide freely longitudinally within lateral deflection Lumen 98 but permits lateral deflection of tip portion 12 by the rotation or torquing of multifunction wire 96.

The size of the curve of tic portion 12 can be adjusted by adjusting how far distal portion 96 extends into tip portion 12. The farther distal portion 96 extends into tip portion 12, the stiffer the tip portion becomes and the smaller the radius of curvature when radial deflection wire 64 is actuated. Typically radial deflection wire 64 is actuated by being pulled; in appropriate circumstances radial deflection wire 64 can be sufficiently stiff so that radial deflection can be achieved by either pulling or pushing on the radial deflection wire 64. As is conventional, thermocouple wires 92 extend to tip electrode 18 to monitor the temperature at the tip electrode while electrode wires 94 extend to the various electrodes 16, 18.

Figure 7:
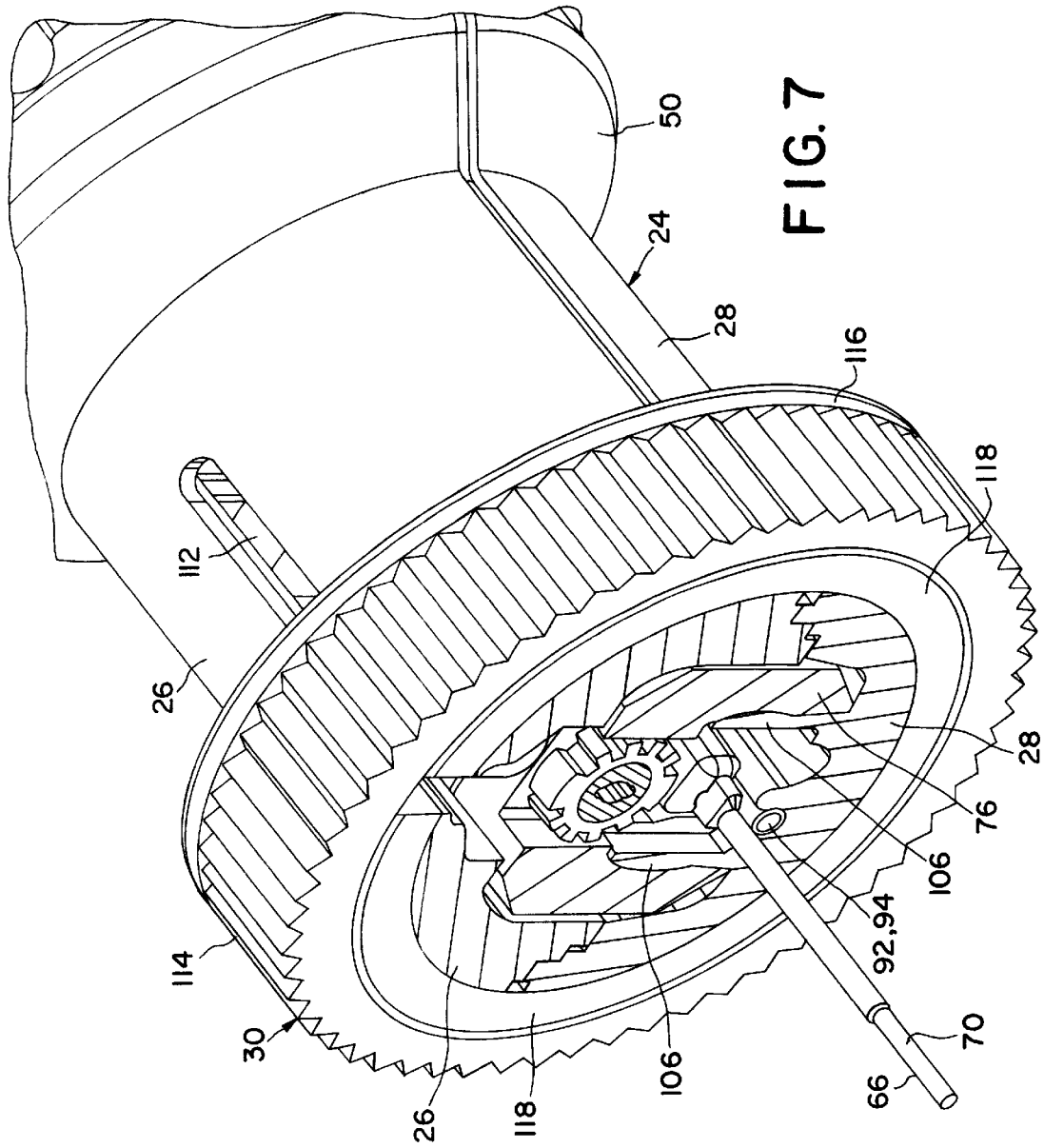
FIG. 7 is an enlarged cross-sectional view taken along line 7—7 of FIG. 1.

FIG. 7 illustrates slider 76 supported by lower body part 28. Slider 78 has a central recess 104, see FIG. 4, with an enlarged upper region sized to snap over and slide along a pair of guide rails 106. A spring-loaded pin 108, see FIG. 2, extends upwardly from a pin housing 110 of slider 76, passes through a longitudinally extending slot 112 formed in upper body part 26 and engages a blind bore, not shown, formed within an interior surface of radial deflection manipulator 30. In this way, longitudinal movement of radial deflection manipulator 30 causes like longitudinal movement of slider 76 and thus of the proximal end 68 of radial deflection wire 64.

Radial deflection manipulator 30 can be secured at any desired position along slot 112. To do so, manipulator 30 includes a serrated ring 114 rotatably mounted about a collet assembly 116. Collet assembly 116 includes a pair of split rings 118. One or both of serrated ring 114 and split rings 118 have cam surfaces so that rotation of serrated ring 114 about hollow body 24 causes split rings 118 to be biased against the outer surface of hollow body 24 thus securing manipulator 30 at the desired longitudinal location.

Figure 8:
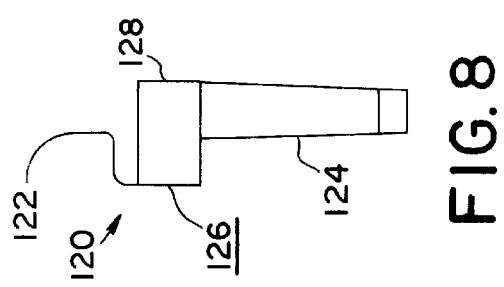
FIG. 8 is an enlarged side view of a stop of FIG. 2.

Longitudinal movement of slider 76 is limited by engagement of pin 108 at either end of slot 112. If desired, this amount of longitudinal movement can be limited in both distal and proximal directions through the use of stops 120. Stops 120, see FIGS. 2 and 8, each have an abutment portion 122 and a pair of legs 124. Each abutment portion 122 has first and second longitudinally-faces 126, 128. Legs 124 are longitudinally offset from the longitudinal center of abutment portion 122. Lower body part 28 has a series of spaced apart positions 130 along its length sized to accept legs 124. Each position 130 is spaced apart by, or example, 2.29 mm (0.090 inch). However, the offset nature of legs 124 changes where faces 126, 128 are positioned even though legs 124 may be located at a particular position 130. In the preferred embodiment the longitudinal position or faces 126, 128 vary by 1.14 mm (0.045 inch) depending upon which face 126, 128 faces in the distal direction. In this way the limit of travel of slider 76 can be adjusted in 1.14 mm increments as opposed to 2.28 mm increments resulting from the 2.28 mm spacing of positions 130 in the preferred embodiment.

Figure 9:
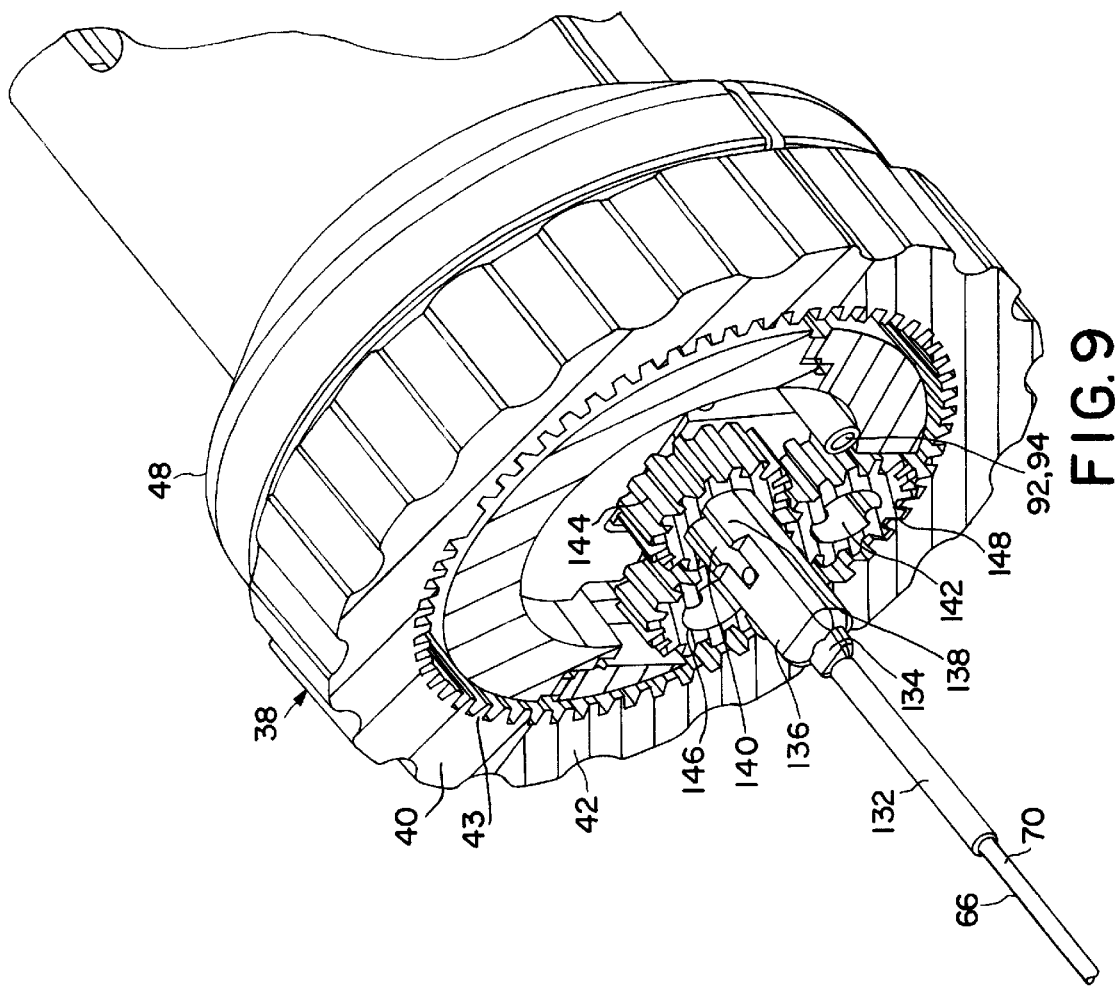
FIG. 9 is an enlarged cross-sectional view taken along line 9—9 of FIG. 1.

FIGS. 2 and 9 illustrate proximal end 70 of multifunction wire 66 having a hypotube segment 132 secured to the proximal end. The hypotube segment 132 has a flattened end 134 which is affixed to an elongate drive adapter 136. The main body 138 (see FIG. 2) of drive adapter 136 has a generally circular cross section but with upper and lower recesses 140 sized to freely slide through a similarly shaped opening 142 formed in a first drive gear 144. As seen in FIG. 9, each gear 144, 146, 148 is identical in construction even though only the first drive gear 144 needs to have the specialized shaped opening 142. Third drive gear 148 engages internal gear 43 and second drive gear 146. Second drive gear 146 acts as an idler gear and transmits motion from third drive gear 148 to first drive gear 144. Therefore, rotating lateral deflection manipulator 38 causes the gear train including internal gear 43 and gears 148, 146, 144 to rotate and thus drive drive adapter 136 about its longitudinal axis thus rotating multifunction wire 66 about its longitudinal axis. This rotation of multifunction wire 66 is relatively free except where flattened distal portion 96 of multifunction wire 66 engages tip portion 12 through interfering torquing surfaces 100, 102.

The proximal end 150 of drive adapter 136 is rotatably coupled to a second slider 76a through a rotary coupling 152. See FIGS. 2 and 4. Rotary coupling 152 is clipped to slider 76a by a pair of clip arms 154. Through clip arms 154 and rotary coupling 152, proximal end 150 of drive adapter 136, and thus proximal end 70 of multifunction wire 66, is free to rotate relative to slider 76a but is not free to move longitudinally relative to slider 76a. The longitudinal position of slider 76a is determined by the position of a curve size manipulator 32, which is substantially identical to radial deflection manipulator 30. Curve size manipulator 32 is coupled to slider 76a by a pin 108a which passes through a slot 112a formed in upper body part 26. Sliders 76 and 76a have specially adapted portions for accommodating connection to the radial deflection wire 64 and multifunction wire 66. Similarly, a pair of stops 120 can be used proximal and distal of slider 76a to limit the longitudinal movement of the slider.

Figure 10:
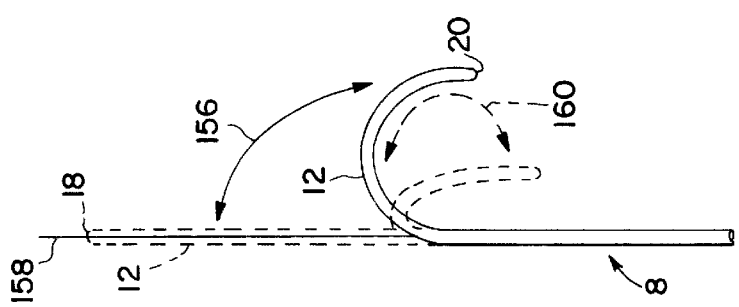
FIG. 10 illustrates the tip portion of the catheter of FIG. 1 after radial deflection, as shown by the solid line arrow and the solid line radially-deflected tip portion, and after in-plane lateral deflection, as illustrated by the dashed line arrow and the dashed line radially- and laterally-deflected tip portion.

During assembly of catheter assembly 2 the limits of movement of sliders 76 and 76a are determined by the placement of stops 120. Undesirable corkscrewing or other deflection of tip portion 12 can be removed, or substancially removed, by rotating adjustment adapter 78 housed within T-slot 84. After these adjustments have been made, upper and lower body parts 26, 28 are secured to one another, typically by ultrasonic welding. During use tip portion 12 can be moved in the direction of arrow 156, from the dashed line position of FIG. 10, aligned with longitudinal axis 158, o the solid line position of FIG. 10 by the movement of radial deflection manipulator 30 in a proximal direction. The size or radius of the curved tip portion 12 of FIG. 10 can be changed by the longitudinal movement of curved size manipulator 32. Radially deflected tip portion 12 can be deflected laterally, that is in the direction of arrow 160, by the rotation of lateral deflection manipulator 38. In the preferred embodiment, through the use of stops 44, 46, lateral deflection manipulator 38 is limited to movement of about 180° in each direction from a neutral or start position. However, by virtue of the gear ratios, one revolution of manipulator 38 results in four revolutions of first gear 44.

Modification and variation can be made to the disclosed embodiment without departing from the subject of the invention as defined in the following claims. For example, instead of gears, friction drive elements could be used. Also, by appropriately positioning first gear 144 adjacent to internal gear 43 of lateral deflection manipulator 38, the need for second and third gears 146, 148 would be eliminated; while a single gear could be used to replace gears 146, 148, doing so would result in a reversal of rotary motion between the lateral deflection manipulator 38 and multifunction wire 66, which is generally not desirable. Other drive schemes could be used to rotate multifunction wire 66; for example, first drive gear 144 could be coupled to manipulator 38 by a drive chain. In some situations a small electric motor could be used to rotate the proximal end 70 of multifunction wire 66. Also, adjustment adapter 78 could be configured differently; for example, instead of using serrations at end 80, cylindrical end 82 could have a hexagonal extension to permit the rotary orientation of adapter 73 to be changed using a wrench or similar tool.

What is claimed is:

1. A catheter assembly comprising:

a proximal end assembly comprising a hollow body;

a catheter extending from the body of the proximal end assembly, the catheter comprising a catheter shaft, having a proximal end and a tip portion, and a manipulator element, having a distal portion coupled to tip portion and a proximal portion extending from the catheter shaft into the hollow body;

the proximal end assembly further comprising:
a manipulator movably mounted to the body;
a rotary coupler connecting the manipulator and the proximal portion of the manipulator element so that movement of the manipulator moves the proximal portion of the manipulator element; and
a radial deflection element having a proximal end coupled to the rotary coupler; and
said rotary coupler comprising means for adjusting the rotary orientation of the proximal end of the radial deflection element relative to the hollow body;

whereby an initial lateral deflection of the tip portion can be removed.

* * * * *

UNITED STATES PATENT AND TRADEMARK OFFICE
CERTIFICATE OF CORRECTION

PATENT NO. : 6,263,224 B1
DATED : July 17, 2001
INVENTOR(S) : Scott H. West

It is certified that error appears in the above-identified patent and that said Letters Patent is hereby corrected as shown below:

Column 6,
Line 53, after the word "element;" delete "and".

Signed and Sealed this

Twenty-eighth Day of January, 2003

JAMES E. ROGAN
*Director of the United States Patent and Trademark Office*